United States Patent
Bradley et al.

(10) Patent No.: US 9,694,134 B2
(45) Date of Patent: Jul. 4, 2017

(54) ASSEMBLY FOR SEQUENTIALLY DELIVERING SUBSTANCES, AND ASSOCIATED METHODS

(71) Applicant: Zoetis Services LLC, Florham Park, NJ (US)

(72) Inventors: Christopher Michael Bradley, Orinda, CA (US); Roland Jeffrey Wyatt, Bozeman, MT (US); Jeffrey Alan Tilley, La Honda, CA (US); Bradley Welding Kolstad, Hackettstown, NJ (US)

(73) Assignee: Zoetis Services LLC, Parsippany, NJ (US)

( * ) Notice: Subject to any disclaimer, the term of this patent is extended or adjusted under 35 U.S.C. 154(b) by 48 days.

(21) Appl. No.: 14/482,556

(22) Filed: Sep. 10, 2014

(65) Prior Publication Data
US 2015/0080841 A1 Mar. 19, 2015

Related U.S. Application Data

(60) Provisional application No. 62/026,936, filed on Jul. 21, 2014, provisional application No. 61/878,162, filed on Sep. 16, 2013.

(51) Int. Cl.
*A61M 5/19* (2006.01)
*A61D 7/00* (2006.01)
(Continued)

(52) U.S. Cl.
CPC ............. *A61M 5/19* (2013.01); *A61D 7/00* (2013.01); *A61M 5/2448* (2013.01);
(Continued)

(58) Field of Classification Search
CPC ............. A61M 5/19; A61M 5/31596; A61M 5/31513; A61M 5/2448; A61M 5/31515; A61M 2005/31598; A61M 2005/1787
See application file for complete search history.

(56) References Cited

U.S. PATENT DOCUMENTS

| 2,159,217 A | 5/1939 | Lozier et al. |
| 2,193,322 A | 3/1940 | Lozier et al. |

(Continued)

FOREIGN PATENT DOCUMENTS

| CA | 2543299 A1 | 5/2005 |
| CN | 202605441 U | 12/2012 |

(Continued)

OTHER PUBLICATIONS

International Search Report and Written Opinion, International Application No. PCT/US2014/051194, date of mailing Oct. 23, 2014.

(Continued)

Primary Examiner — Bradley Osinski
(74) Attorney, Agent, or Firm — Scott C. Mayhew

(57) ABSTRACT

An infusion assembly is provided. Such an infusion assembly includes a first infusion body and a first nozzle operably engaged with the first infusion body. A first plunger is configured to translate longitudinally within the first infusion body for dispensing a first substance out of the first infusion body through the first nozzle. The plunger has a translating member and a stopper piston separable and removable from the translating member. Once separated, the stopper piston is capable of receiving a second nozzle of a second infusion body such that the first substance, along with a second substance in the second infusion body, are capable of being sequentially administered to a target site. An associated method and kit are also provided.

14 Claims, 18 Drawing Sheets

(51) Int. Cl.
*A61M 5/24* (2006.01)
*A61M 5/315* (2006.01)
*A61M 5/42* (2006.01)
*A61M 5/178* (2006.01)

(52) U.S. Cl.
CPC .... *A61M 5/31513* (2013.01); *A61M 5/31596* (2013.01); *A61M 5/422* (2013.01); *A61M 5/31515* (2013.01); *A61M 2005/1787* (2013.01); *A61M 2005/31598* (2013.01)

(56) References Cited

U.S. PATENT DOCUMENTS

| | | |
|---|---|---|
| 2,687,728 A | 8/1954 | Copen |
| 2,939,459 A | 6/1960 | Lazarte et al. |
| 3,346,147 A | 10/1967 | Higgins et al. |
| 3,563,240 A | 2/1971 | Silver |
| 3,749,084 A | 7/1973 | Cucchiara |
| 3,766,917 A | 10/1973 | Wimmer |
| 3,911,916 A | 10/1975 | Stevens |
| 3,923,058 A | 12/1975 | Weingarten |
| 3,986,645 A | 10/1976 | Baldwin et al. |
| 4,188,949 A | 2/1980 | Antoshkiw |
| 4,313,440 A | 2/1982 | Ashley |
| 4,394,863 A | 7/1983 | Bartner |
| 4,439,184 A | 3/1984 | Wheeler |
| 4,702,737 A | 10/1987 | Pizzino |
| 5,026,346 A | 6/1991 | Spanner et al. |
| 5,102,388 A | 4/1992 | Richmond |
| 5,279,606 A | 1/1994 | Haber et al. |
| 5,298,024 A | 3/1994 | Richmond |
| 5,415,648 A | 5/1995 | Malay et al. |
| 5,476,449 A | 12/1995 | Richmond |
| 5,520,657 A | 5/1996 | Sellers et al. |
| 5,704,918 A | 1/1998 | Higashikawa |
| 5,720,731 A | 2/1998 | Aramata et al. |
| 6,077,252 A | 6/2000 | Siegel |
| 6,149,628 A | 11/2000 | Szapiro et al. |
| 6,440,101 B1 | 8/2002 | Grabenkort et al. |
| 6,458,095 B1 | 10/2002 | Wirt et al. |
| 6,558,358 B2 | 5/2003 | Rosoff et al. |
| 6,723,074 B1 | 4/2004 | Halseth |
| 6,802,822 B1 | 10/2004 | Dodge |
| 6,866,653 B2 | 3/2005 | Bae |
| 7,011,650 B2 | 3/2006 | Rosoff et al. |
| 7,828,765 B2 | 11/2010 | Hallahan et al. |
| 8,353,877 B2 | 1/2013 | Hallahan et al. |
| 2002/0068910 A1 | 6/2002 | Szapiro et al. |
| 2002/0198490 A1 | 12/2002 | Wirt et al. |
| 2003/0060414 A1 | 3/2003 | McHardy et al. |
| 2003/0236503 A1 | 12/2003 | Koenig et al. |
| 2004/0044316 A1 | 3/2004 | Greenfield |
| 2004/0116871 A1 | 6/2004 | Vincent |
| 2005/0245880 A1 | 11/2005 | Howlett et al. |
| 2006/0052747 A1 | 3/2006 | Nishimura et al. |
| 2007/0264310 A1* | 11/2007 | Hissong ............ A61F 11/002 424/437 |
| 2008/0208137 A1 | 8/2008 | Fago |
| 2010/0286513 A1* | 11/2010 | Pollard, Jr. ........ A61M 5/31511 600/432 |
| 2011/0160674 A1 | 6/2011 | Holmes et al. |
| 2012/0323173 A1* | 12/2012 | Thorne, Jr. ....... A61M 5/31596 604/89 |
| 2014/0276630 A1 | 9/2014 | Pokorney et al. |

FOREIGN PATENT DOCUMENTS

| | | |
|---|---|---|
| DE | 2514201 A1 | 10/1976 |
| DE | 10110126 A1 | 9/2002 |
| EP | 0082251 | 9/1982 |
| EP | 0078899 A1 | 5/1983 |
| EP | 0737484 A2 | 10/1996 |
| EP | 2620124 A1 | 7/2013 |
| FR | 2076853 | 10/1971 |
| FR | 2251339 | 6/1975 |
| FR | 2506161 | 11/1982 |
| FR | 2573310 | 5/1986 |
| FR | 2750051 A1 | 12/1997 |
| GB | 1441747 | 7/1976 |
| GB | 2376048 A | 12/2002 |
| JP | 58-133260 | 8/1983 |
| JP | 8294532 A2 | 11/1996 |
| JP | 2003-299734 A | 10/2003 |
| WO | WO 91/16094 A1 | 10/1991 |
| WO | WO 94/13261 A1 | 6/1994 |
| WO | WO 95/31180 A1 | 11/1995 |
| WO | WO 98/26759 A1 | 6/1998 |
| WO | WO 99/17820 A1 | 4/1999 |
| WO | WO 02/11793 A1 | 2/2002 |
| WO | WO 02/072171 A2 | 9/2002 |
| WO | WO 2004/039434 A2 | 5/2004 |
| WO | WO 2005/072644 A1 | 8/2005 |
| WO | WO 2007/006030 A3 | 1/2007 |
| WO | WO 2009/094345 A1 | 7/2009 |
| WO | WO 2013/021186 A1 | 2/2013 |
| WO | WO 2014/001353 A1 | 1/2014 |

OTHER PUBLICATIONS

Canadian Office Action, Canadian Patent Application No. 2,923,555.

* cited by examiner

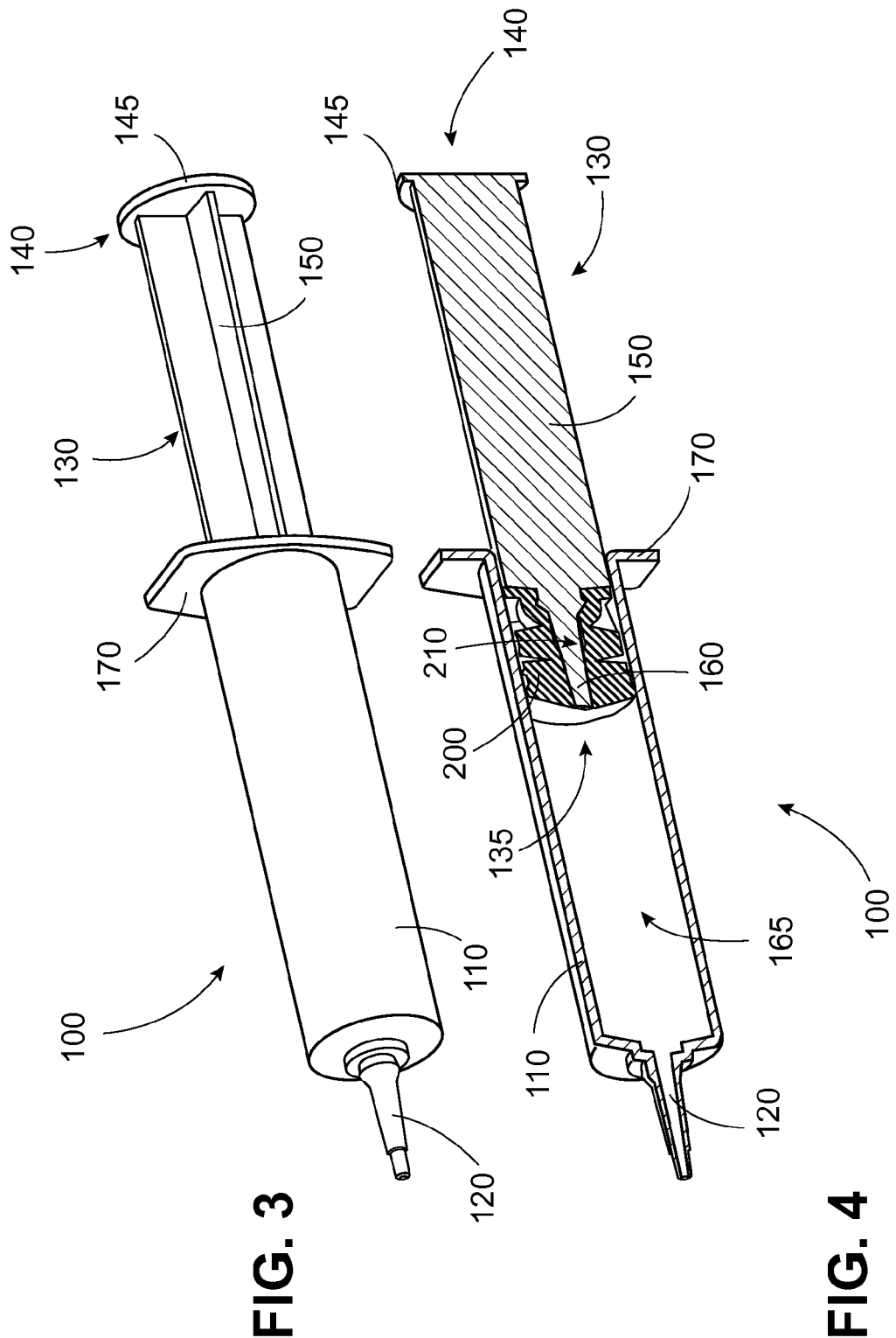

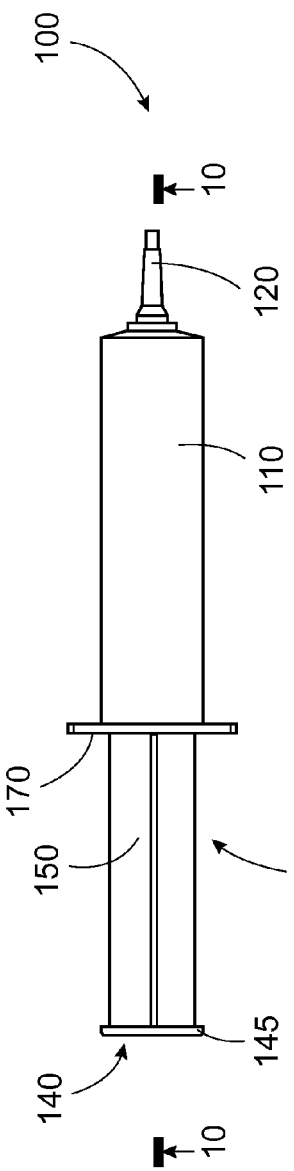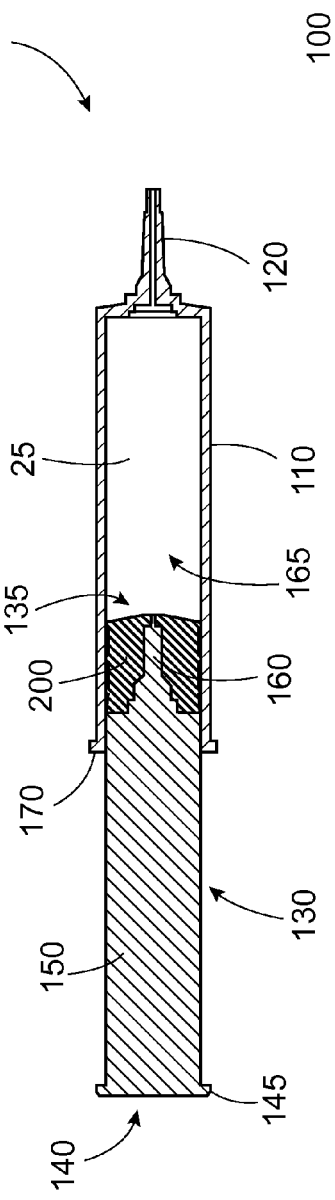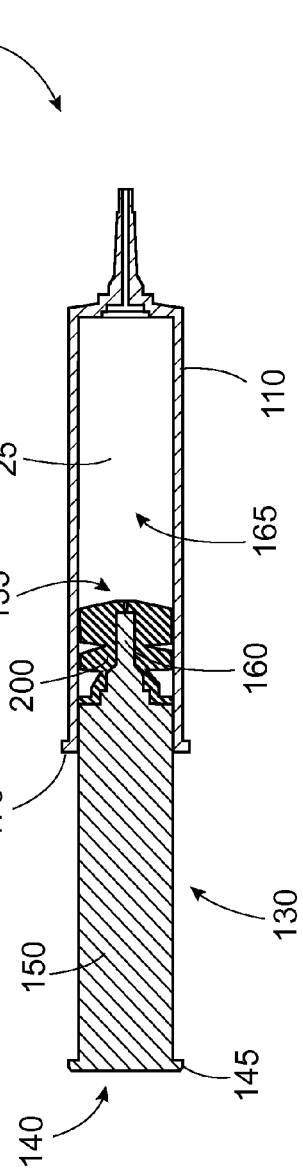

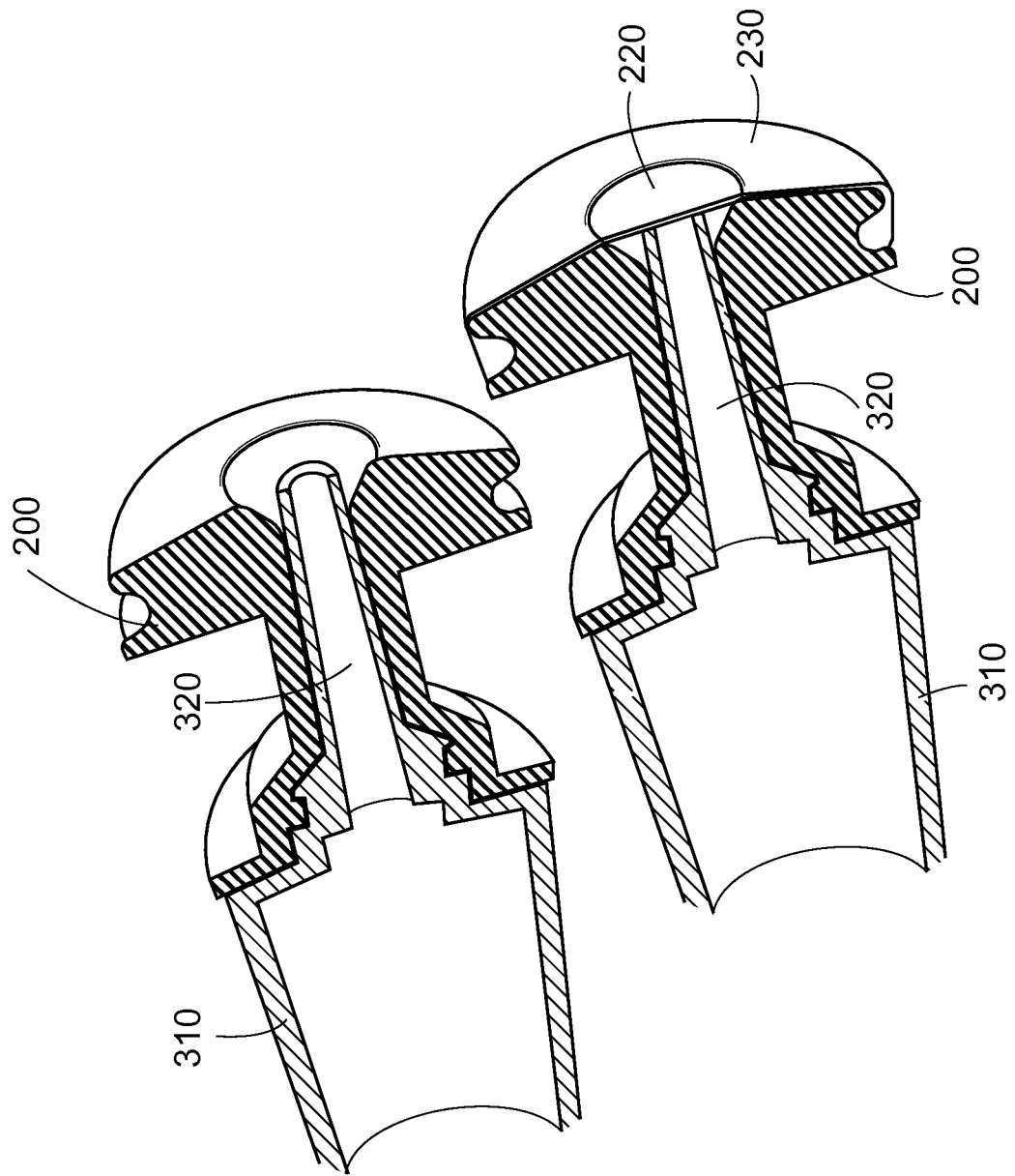

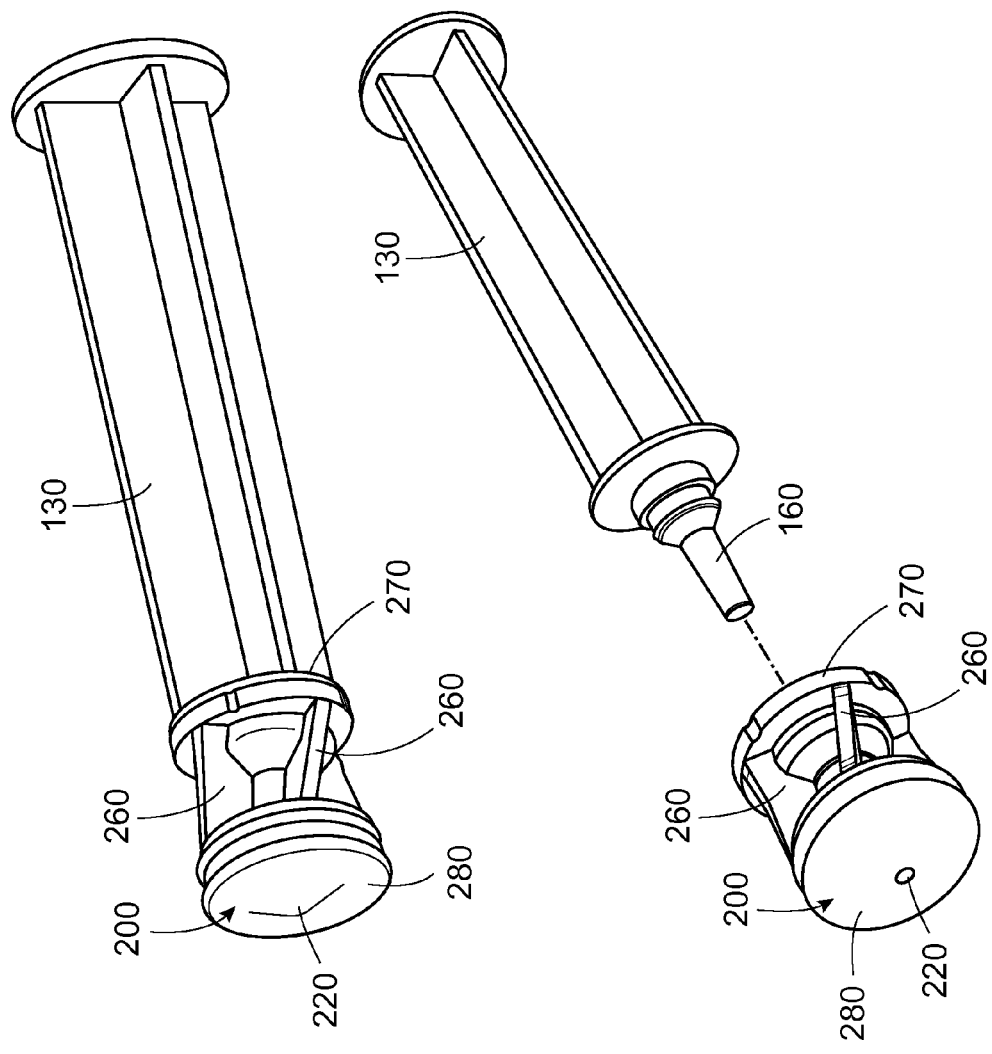

ASSEMBLY FOR SEQUENTIALLY DELIVERING SUBSTANCES, AND ASSOCIATED METHODS

CROSS REFERENCE TO RELATED APPLICATIONS

This application claims the benefit of U.S. Provisional Patent Application Nos. 61/878,162, filed Sep. 16, 2013, and 62/026,936, filed Jul. 21, 2014, both of which are expressly incorporated herein by reference in their entirety.

TECHNICAL FIELD

The present disclosure generally relates to infusion devices for sequentially infusing substances into a target site. More particularly, the present disclosure relates to a co-administration assembly for sequentially infusing a plurality of substances into a target site, and an associated method.

BACKGROUND

Infusion devices are used throughout many industries to infuse a substance into a target site. One particular industry implementing infusion devices to deliver substances is veterinary medicine. For example, multiple infusion devices may be used during a so-called "dry cow program" to successively infuse substances into the udder of a cow so as to treat, control or otherwise limit the onset of bovine mastitis, i.e., the inflammation of udder tissue in cows. In such instances, a typical treatment (a so-called "dry-off procedure") may include infusing multiple substances in succession into the teat canal of a cow, with each substance being infused using its own separate infusion device.

For example, an antimicrobial substance is first infused into the udder using a first infusion device, which is followed by a teat sealant substance being infused into the udder using a second infusion device. Between infusions, a worker must disinfect the cow teat, grab the second infusion device, and insert the second infusion device into the teat canal. Implementing two separate insertion steps into the teat canal can lead to potential issues with contamination between substance insertion if not administered properly. In this regard, the dry-off procedure is time-consuming and administratively difficult since disinfection and cleanliness are paramount.

Previous sequential delivery devices for treating bovine mastitis are single-formed devices. That is, the devices are not capable of being separated to discretely administer the antimicrobial and teat sealant substances. Such single-formed devices can present issues with regard to sterilization of the substances. In this regard, sterilization of the substances may occur after the substances have been incorporated into the devices. Sterilization of the teat sealant substance may be performed at much higher gamma radiations levels than that of the antimicrobial. In a single-formed device, such sterilization at levels necessary to sterilize the teat sealant may undesirably render the antimicrobial substance inactive.

Accordingly, it would be desirable to provide an infusion assembly capable of administering multiple substances into the cow teat following a single insertion into the teat canal, so as to lessen the chance of contamination. Such an assembly may desirably allow a worker to administer both the antimicrobial and teat sealant substances more efficiently by skipping difficult and time-consuming steps. Such an assembly may also be capable of facilitating individual use for each substance such that previous dry-off procedures could be practiced, if desired, which would also allow for individual sterilization of the substances. Furthermore, it would be desirable to provide an associated method of sequentially delivering substances into a target site using an infusion assembly.

BRIEF SUMMARY

The above and other needs are met by aspects of the present disclosure which, according to one aspect, provides an infusion assembly having a first infusion body and a first nozzle operably engaged with the first infusion body. A first plunger is configured to translate longitudinally within the first infusion body for dispensing a first substance out of the first infusion body through the first nozzle. The plunger includes a translating member and a stopper piston separable and removable from the translating member. The stopper piston is configured to facilitate a two-stage seating arrangement.

The above and other needs are met by aspects of the present disclosure which, according to one aspect, provides an infusion assembly having a first infusion body and a first nozzle operably engaged with the first infusion body. A first plunger is configured to translate longitudinally within the first infusion body for dispensing a first substance out of the first infusion body through the first nozzle. The plunger includes a translating member and a stopper piston separable and removable from the translating member.

According to some aspects, the infusion assembly has a second infusion body configured to be received within the first infusion body. A second nozzle is operably engaged with the second infusion body. A second plunger is configured to translate longitudinally within the second infusion body for dispensing a second substance out of the second infusion body through the second nozzle. The stopper piston, once separated from the translating member, is configured to receive the second nozzle such that the second plunger is capable of advancing the stopper piston to dispense the first substance from the first infusion body. The second plunger is capable of being further advanced to dispense a second substance from the second infusion body through the second nozzle and then through the first nozzle.

Another aspect provides a method of sequentially delivering a first and second substance to a target site. The method comprises providing a first infusion device having a first infusion body containing a first substance. The method further comprises providing a second infusion device having a second infusion body containing a second substance. The method further comprises positioning at least a portion of the second infusion device within the first infusion body. The second infusion device has a stopper piston removably engaged with a second nozzle thereof such that the second nozzle extends at least partially therethrough. The method further comprises advancing a plunger associated with the second infusion device such that the stopper piston interacts with the first substance so as to expel the first substance from the first infusion body through a first nozzle of the first infusion device. The method further comprises advancing the plunger so as to expel the second substance from the second infusion body through the second nozzle and then through the first nozzle to a target site.

Yet another aspect provides a kit having a first infusion device having a first substance, a second infusion device having a second substance and a nozzle, and a stopper piston configured to securely receive the nozzle. According to one aspect, the stopper piston has a penetrable portion and is compressible, wherein the stopper piston is configured to collapse such that the penetrable portion is capable of being pierced by the nozzle.

Another aspect provides a method of treatment for bovine mastitis. The method comprises inserting a nozzle of an infusion assembly into a bovine teat canal, wherein the infusion assembly is configured to successively infuse an antimicrobial substance and a teat sealant substance into the bovine teat canal. The method further comprises advancing a plunger to infuse the antimicrobial substance into the bovine teat canal. The method further comprises maintaining the nozzle of the infusion assembly within the bovine teat canal. The method further comprises advancing the plunger to infuse the teat sealant substance into the bovine teat canal.

Thus, various aspects of the present disclosure provide advantages, as otherwise detailed herein.

BRIEF DESCRIPTION OF THE DRAWINGS

Figure 1:
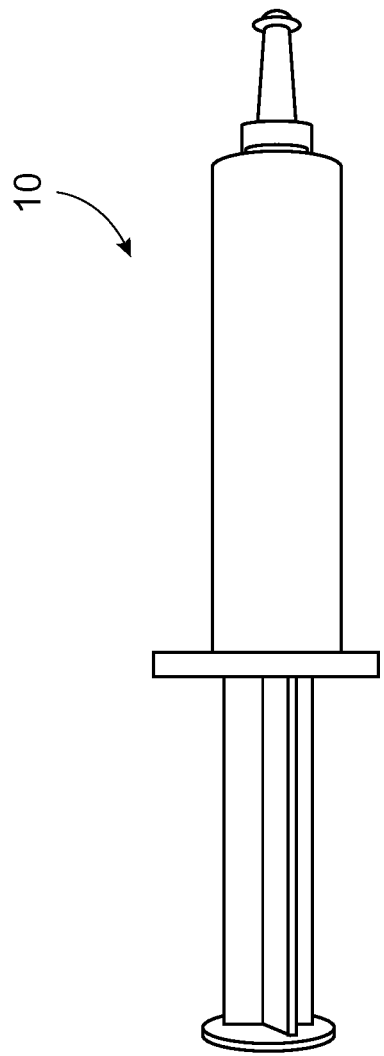
Figure 2:
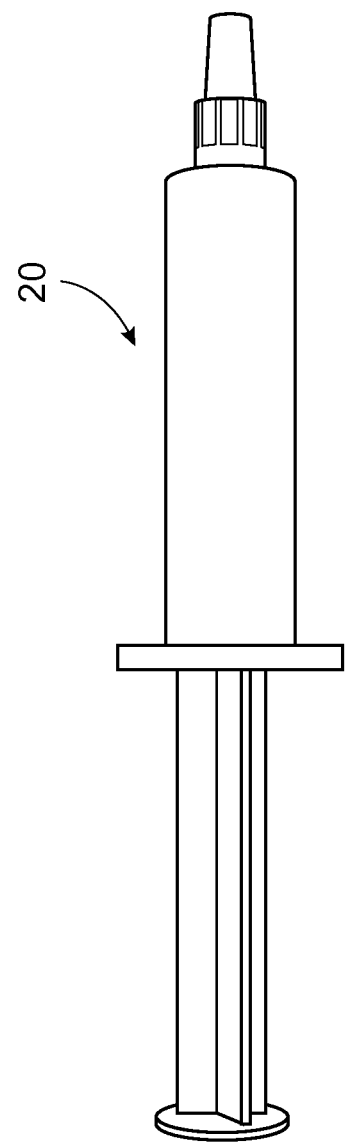
Figure 5:
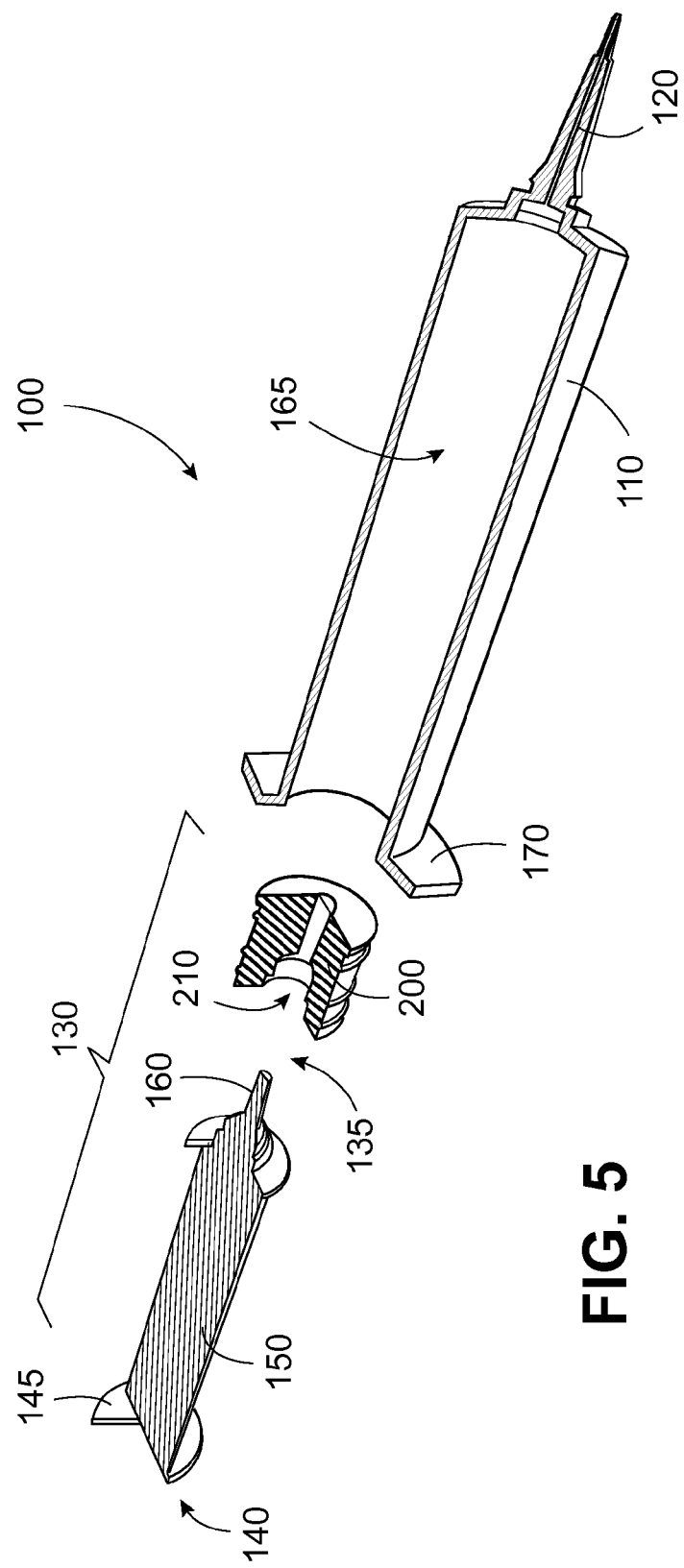
Figure 7:
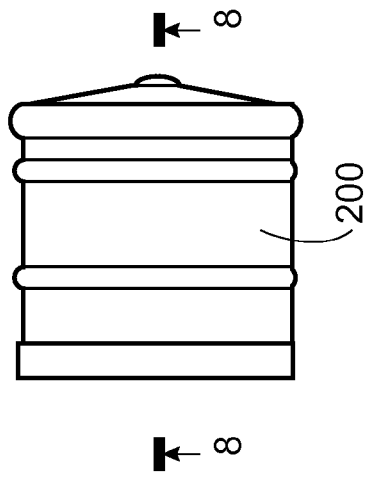
Figure 8:
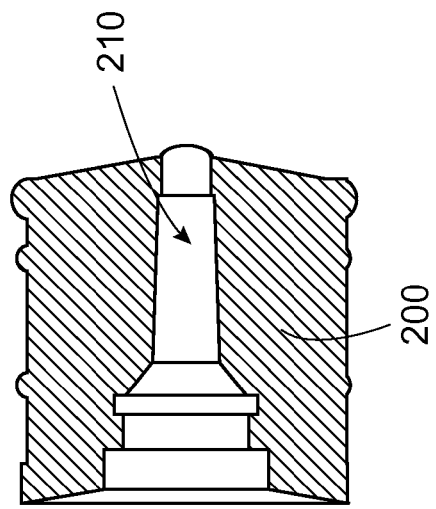
Figure 6:
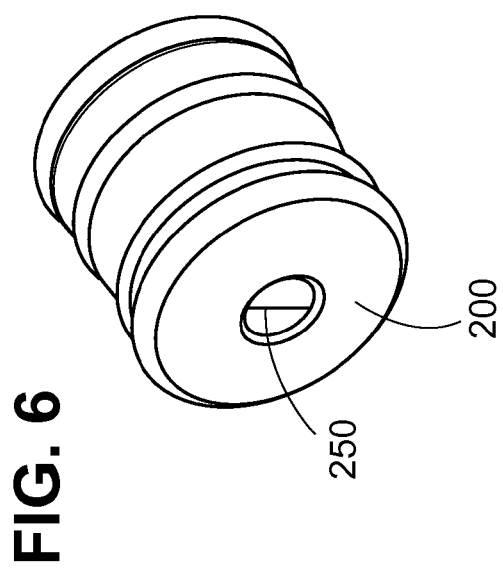
Figures 12, 13:
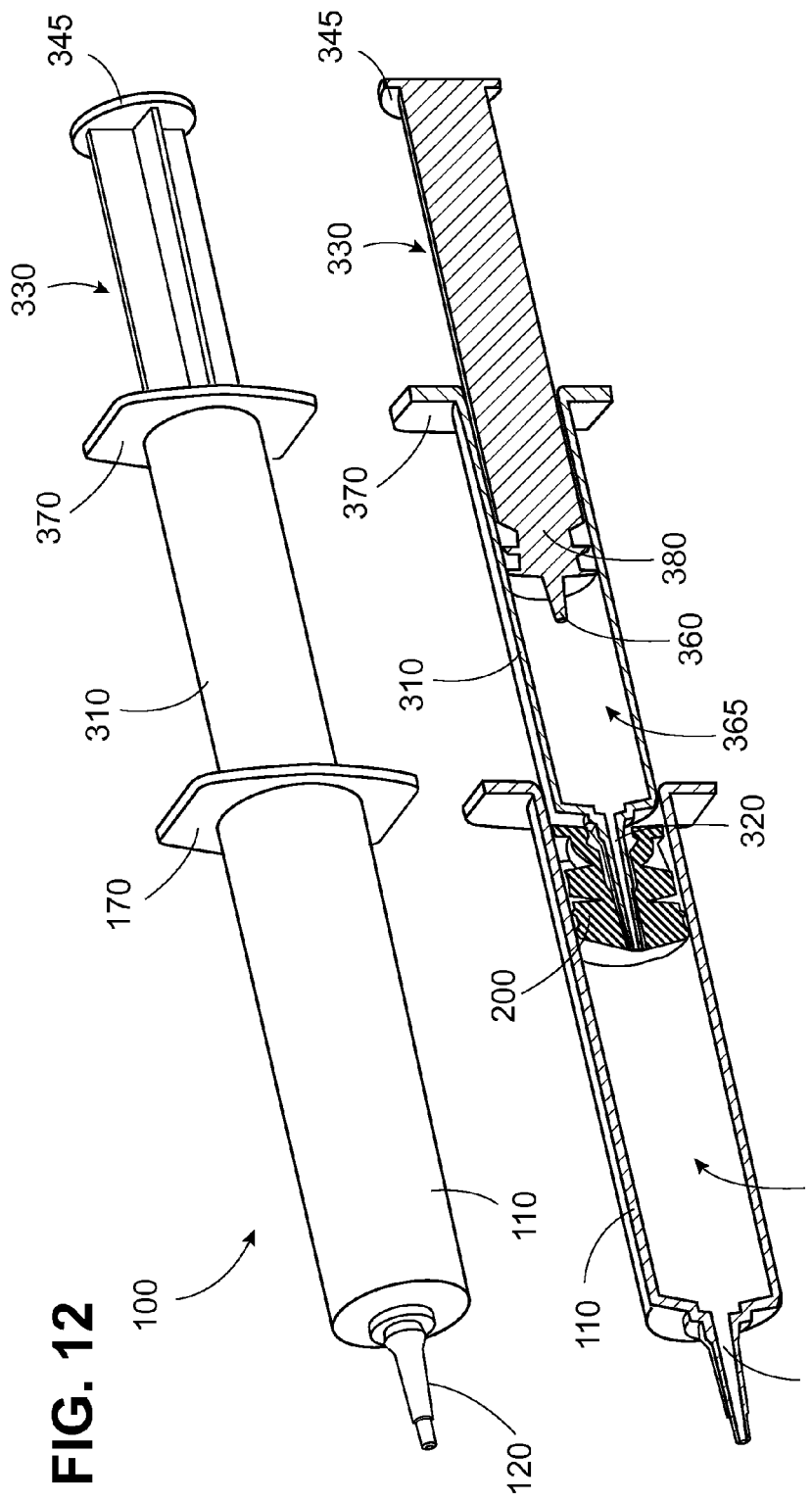
Figure 14:
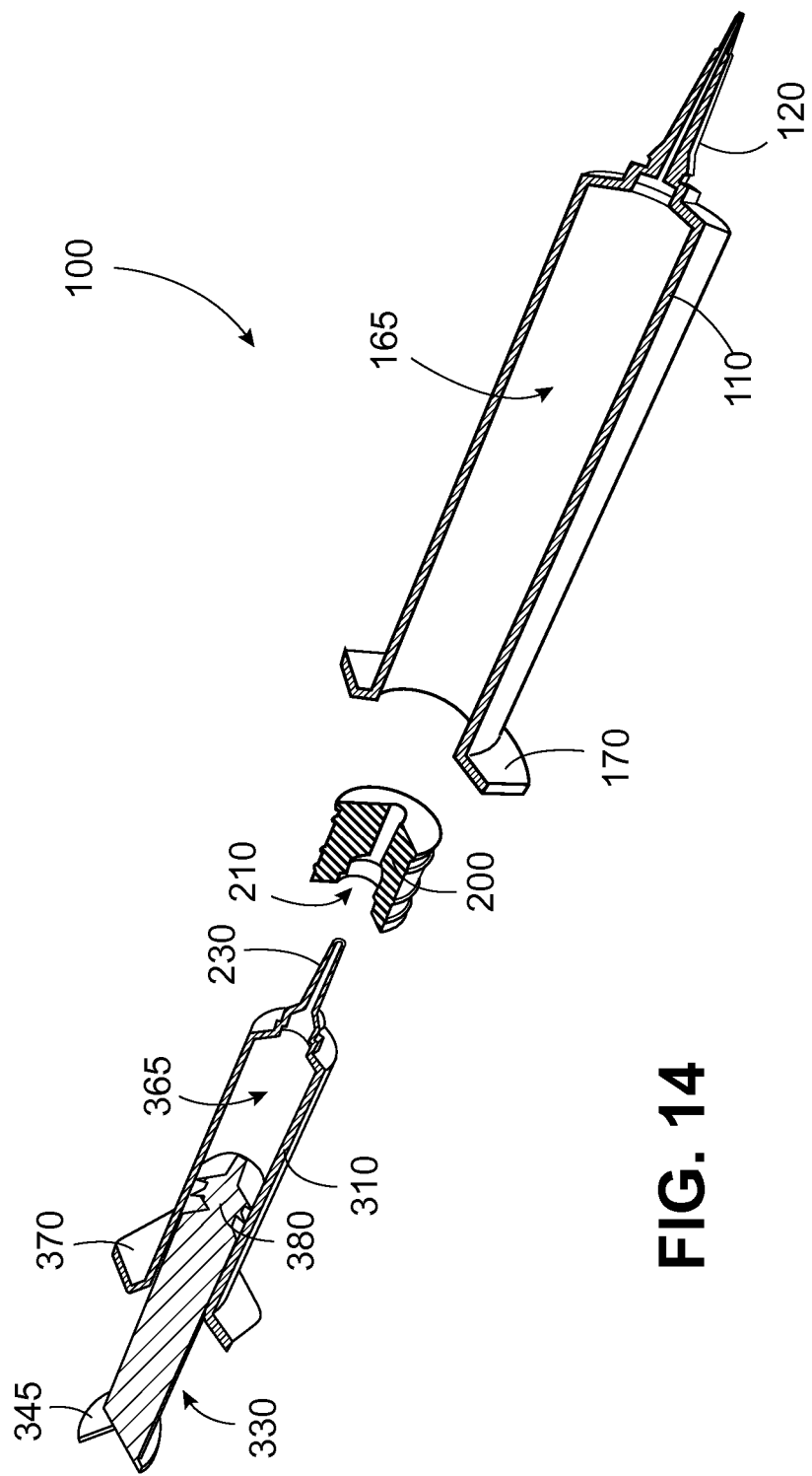
Figure 15:
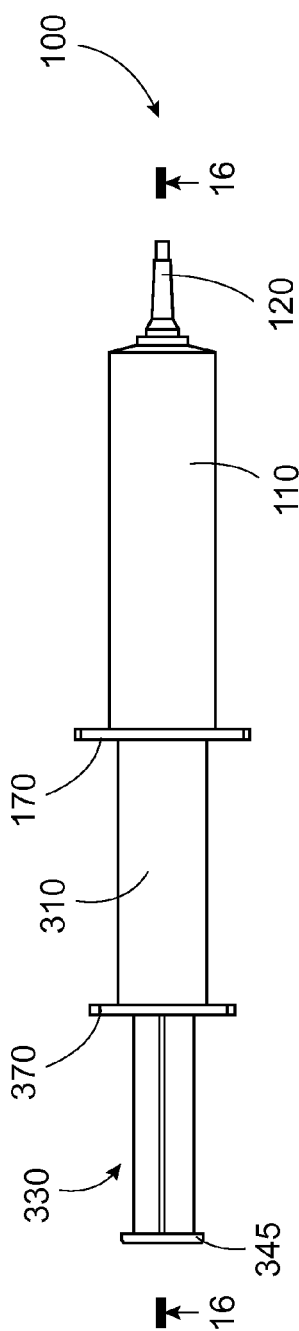
Figure 16:
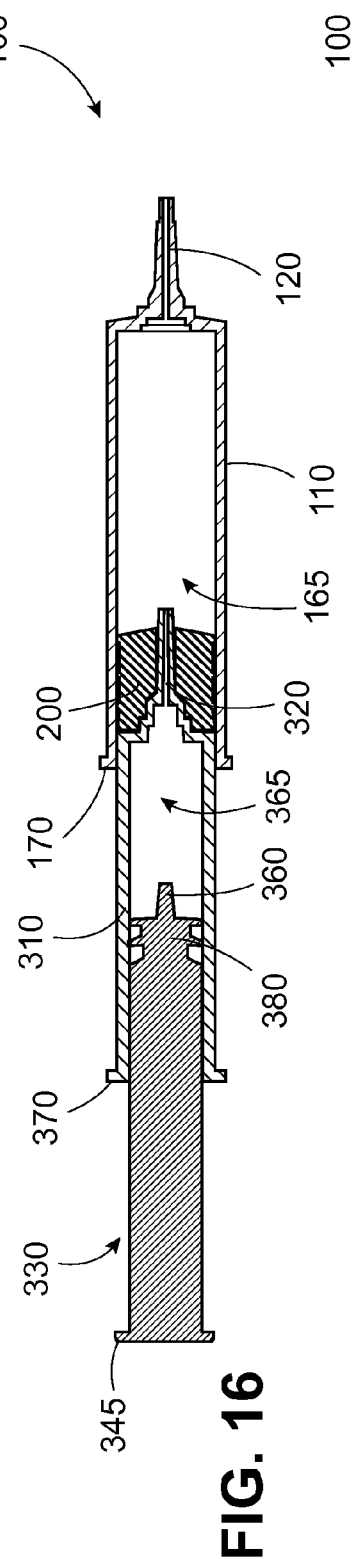
Figure 17:
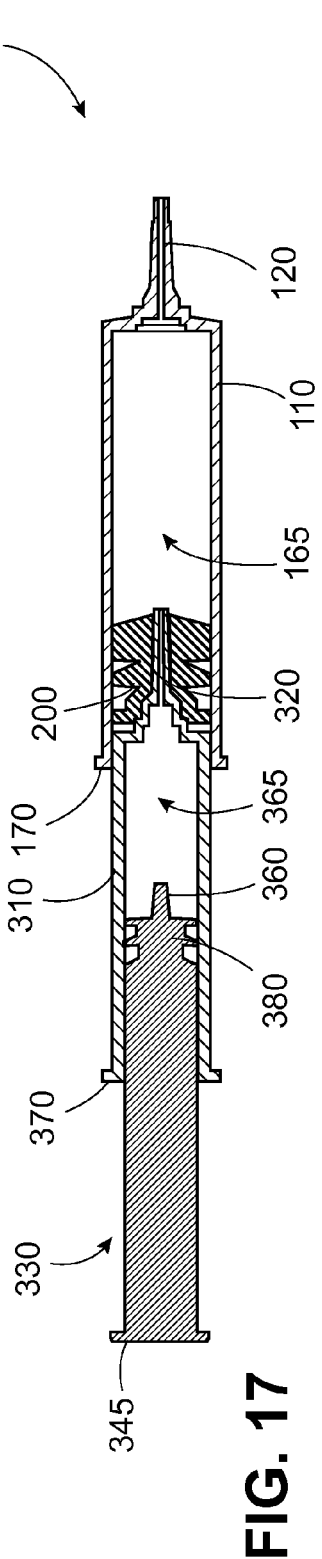
Figure 18:
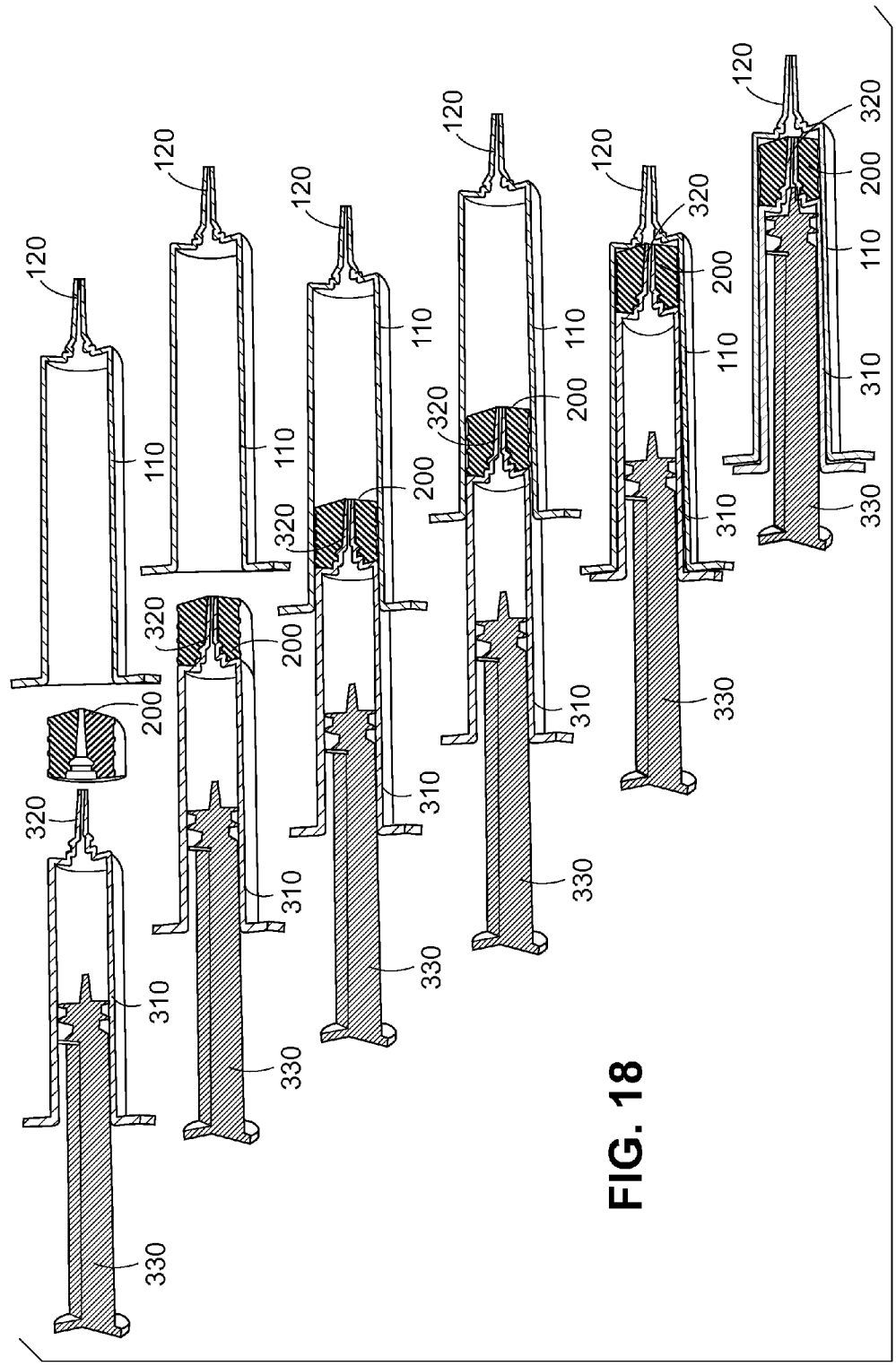
Figure 19:
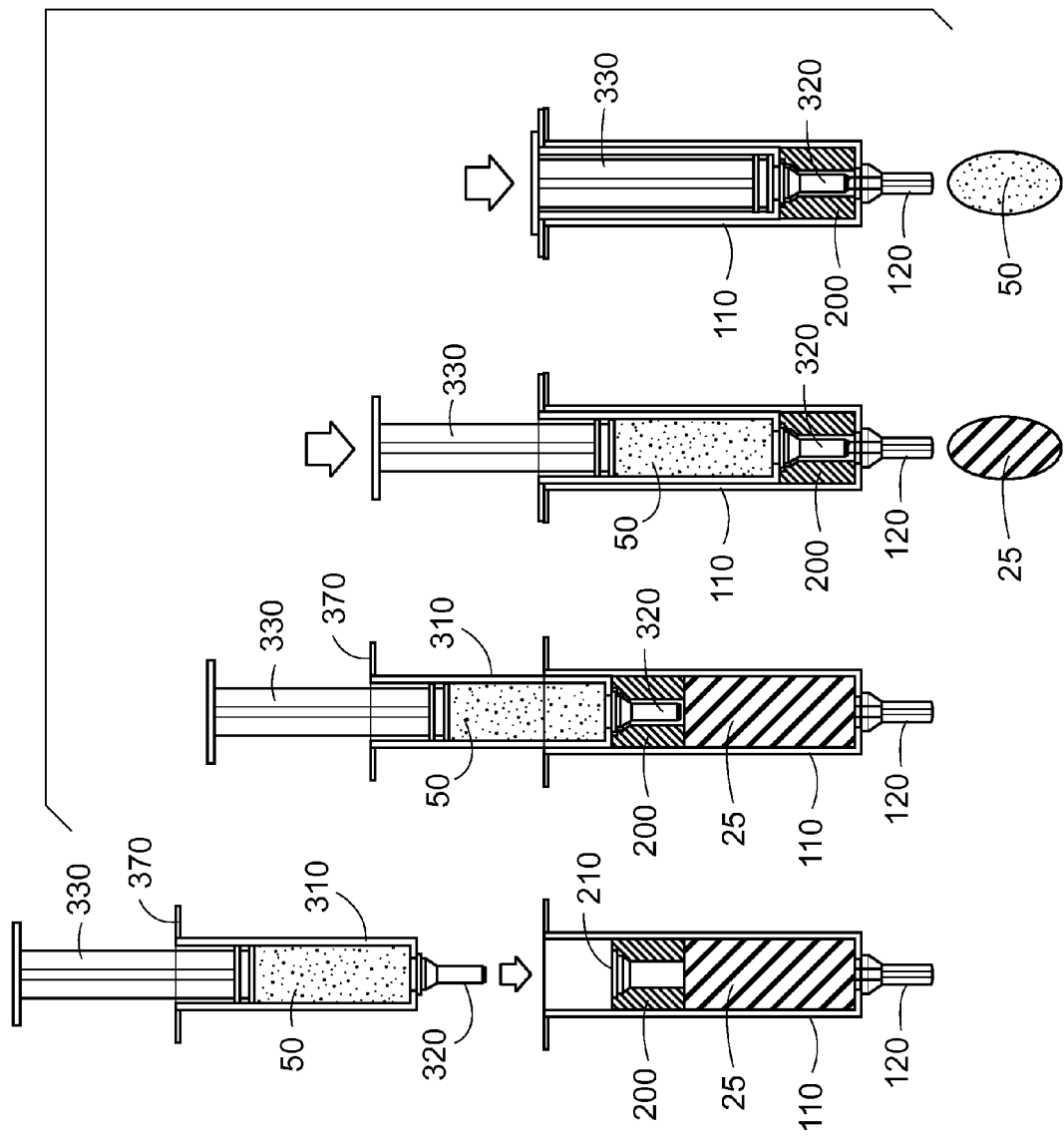
Figure 20:
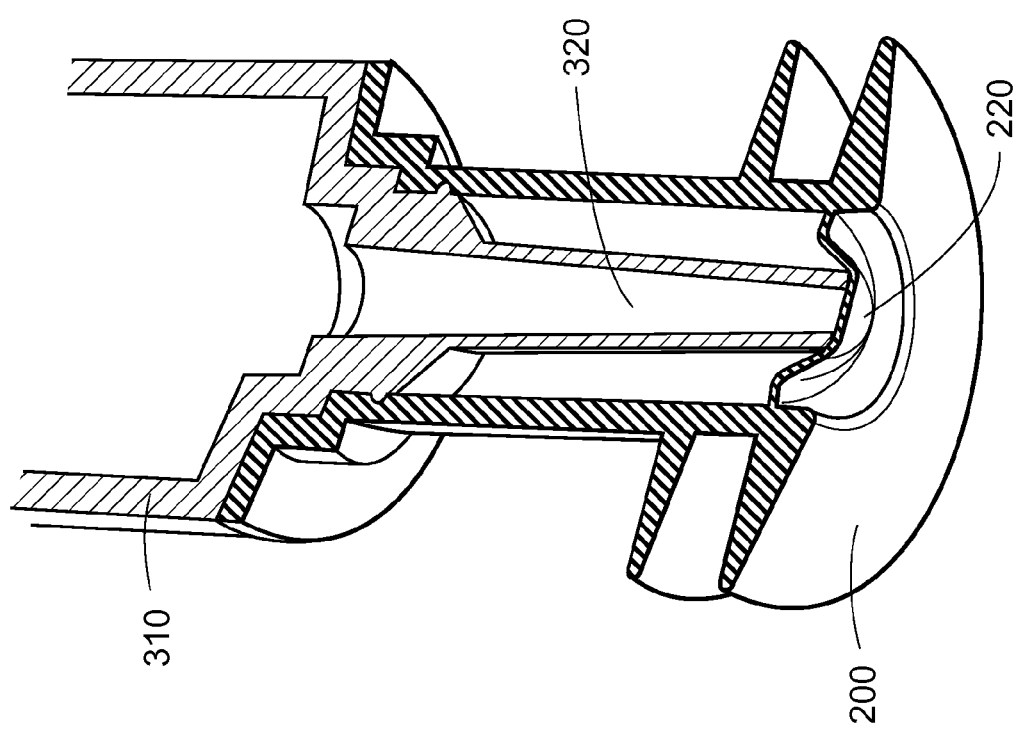
Figure 25:
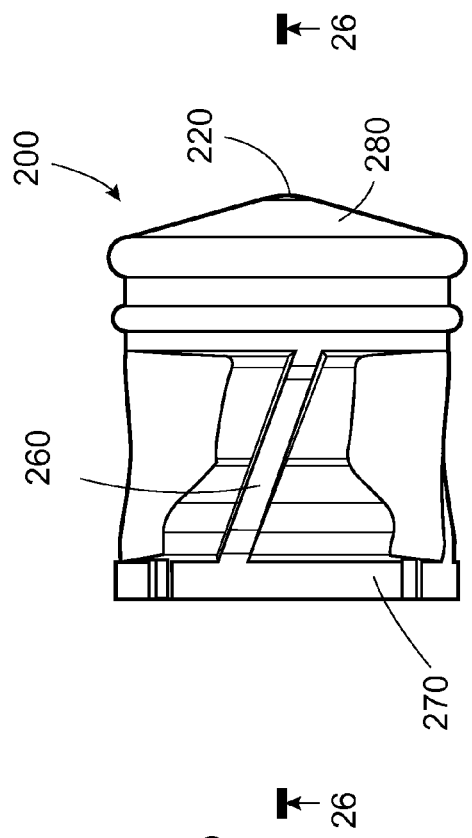
Figure 26:
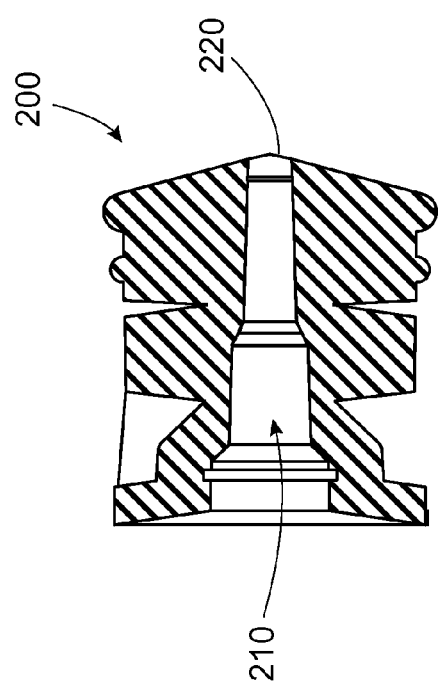
Figures 27, 28:
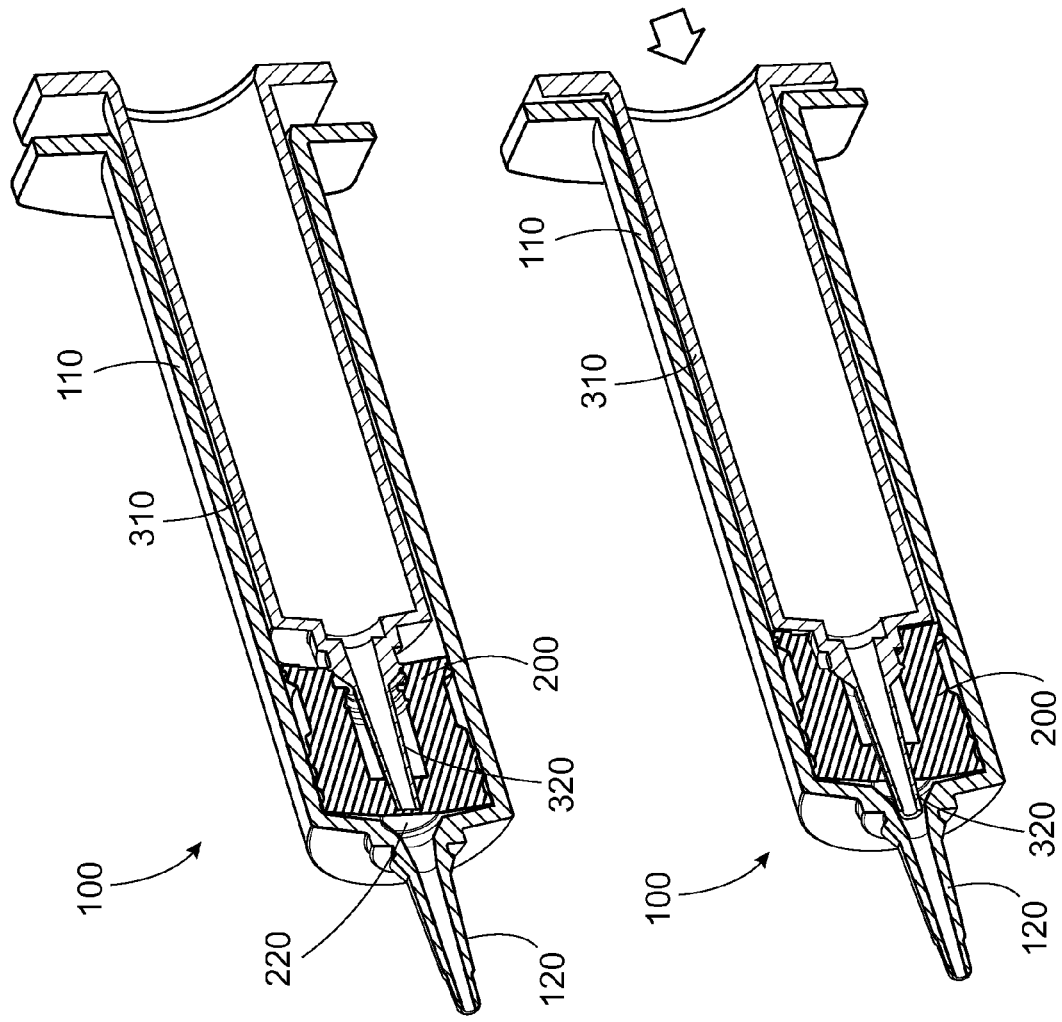
Figure 29:
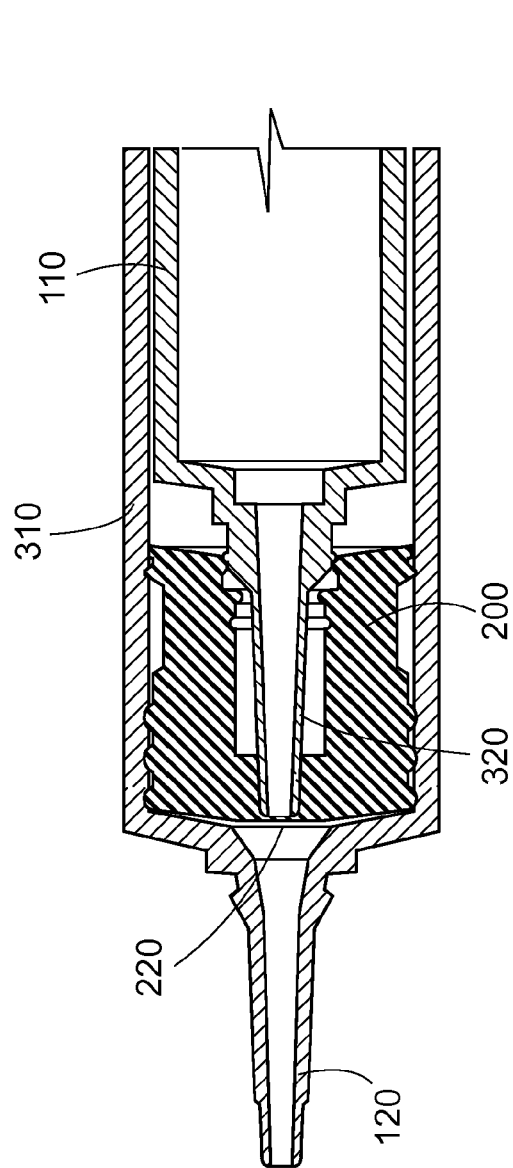
Figure 30:
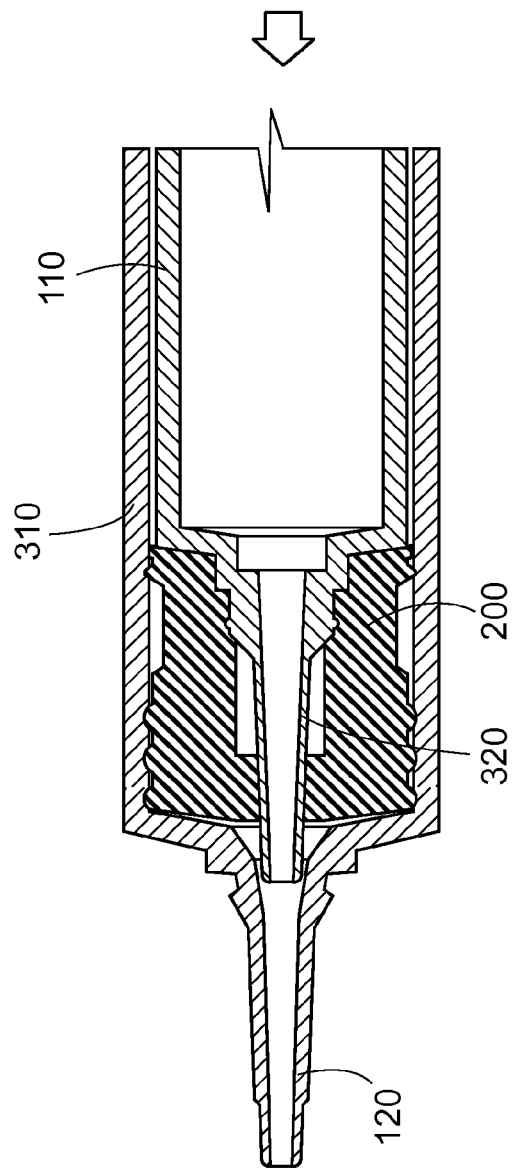
Figure 31:
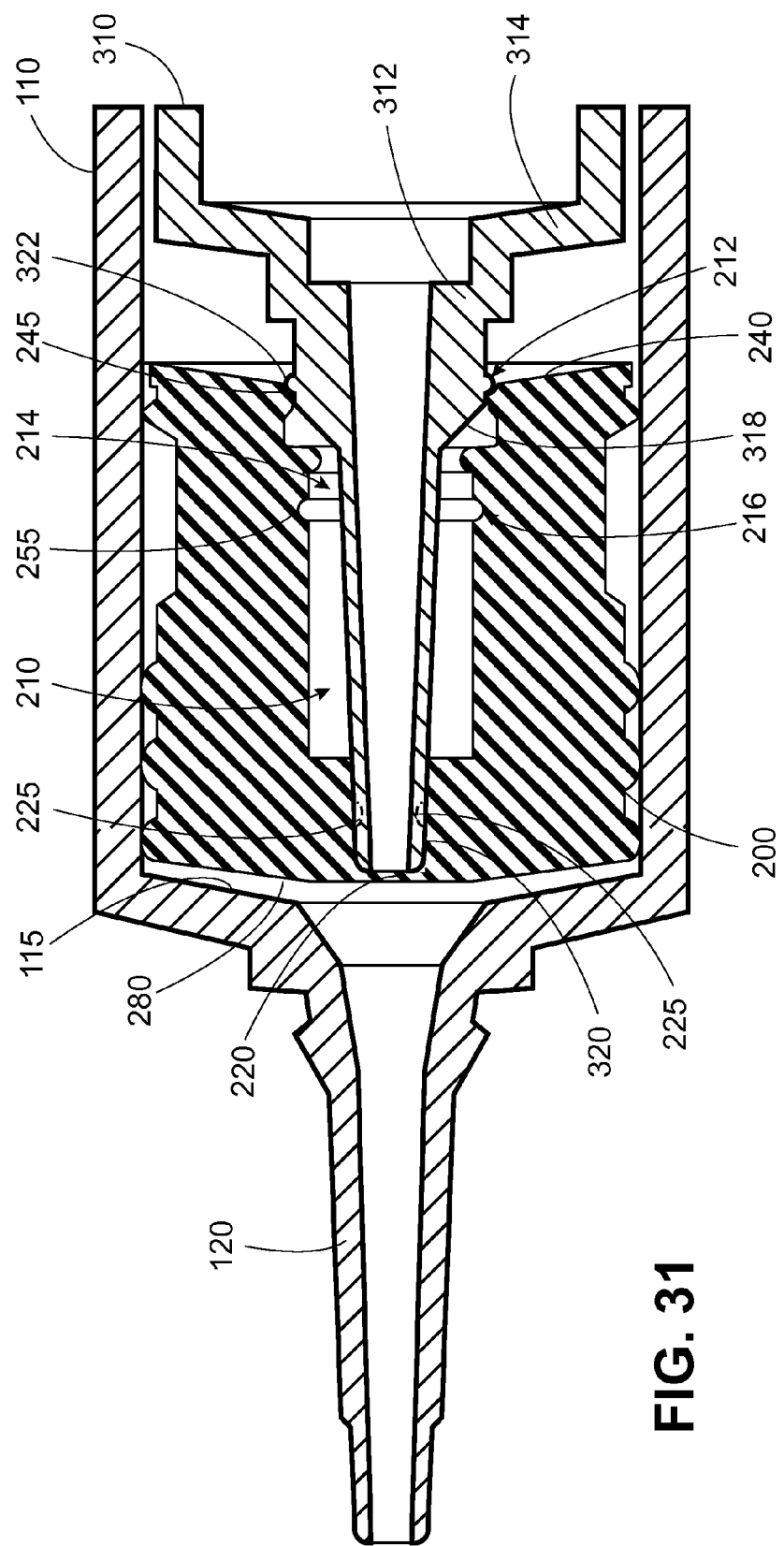
Figure 32:
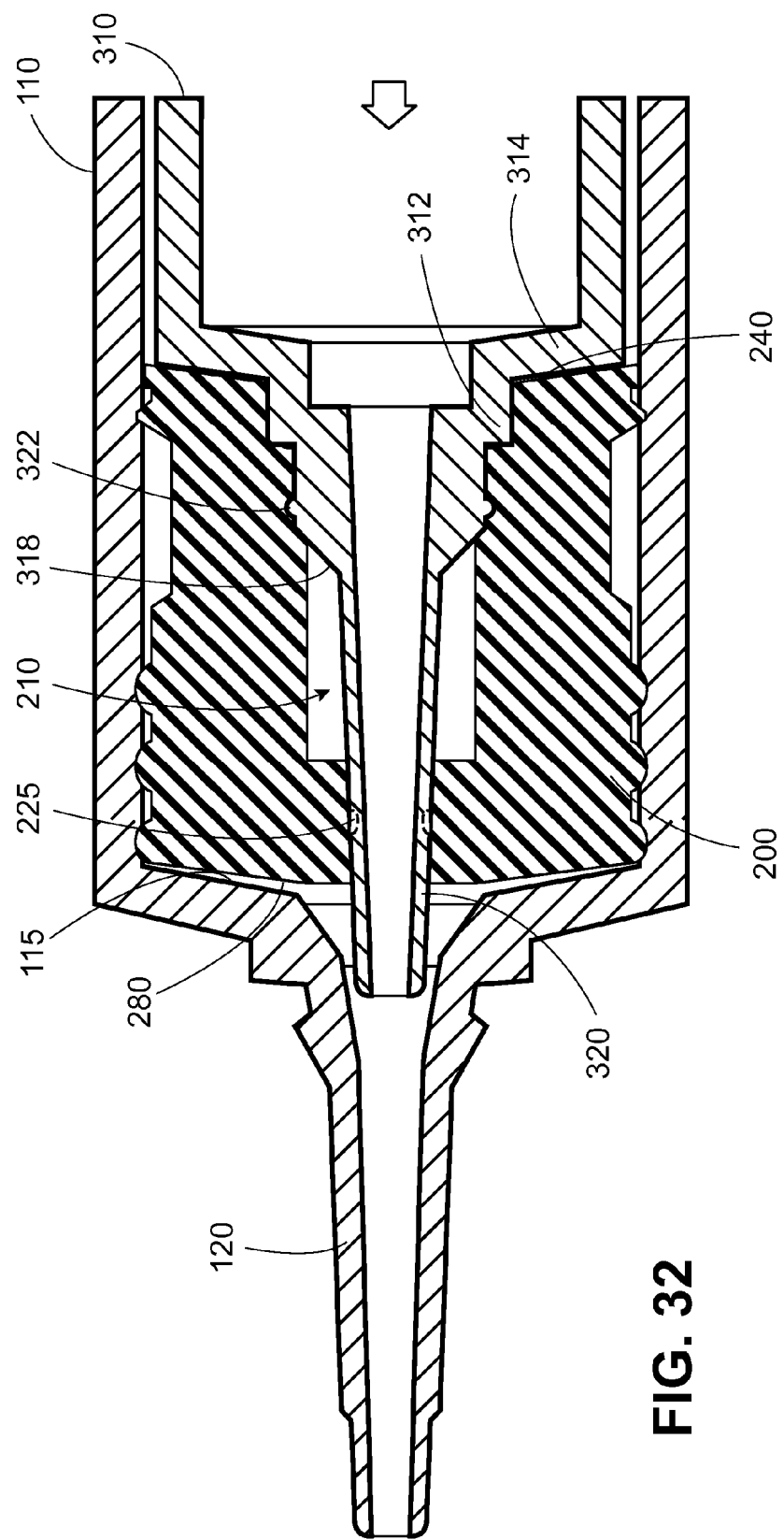

Having thus described various embodiments of the present disclosure in general terms, reference will now be made to the accompanying drawings, which are not necessarily drawn to scale, and wherein:

FIG. 1 is a perspective view of a first infusion device;

FIG. 2 is a perspective view of a second infusion device;

FIG. 3 is a schematic perspective view of an infusion assembly capable of administering a single substance, according to one aspect of the present disclosure;

FIG. 4 is a cross-sectional schematic perspective view of the infusion assembly of FIG. 3;

FIG. 5 is an exploded, sectional schematic perspective view of the infusion assembly of FIG. 3;

FIG. 6 is a schematic perspective view of a stopper piston used with an infusion assembly, according to one aspect of the present disclosure;

FIG. 7 is a schematic side view of the stopper of FIG. 6;

FIG. 8 is a cross-sectional view of the stopper of FIG. 7 taken along the line 8-8;

FIG. 9 is a schematic side view of an infusion assembly, according to one aspect of the present disclosure;

FIG. 10 a cross-sectional schematic view of the infusion assembly taken along the line 10-10 of FIG. 9, illustrating a stopper piston arrangement;

FIG. 11 is a cross-sectional schematic view of the infusion assembly taken along the line 10-10 of FIG. 9, illustrating an alternative stopper arrangement;

FIG. 12 is a schematic perspective view of an infusion assembly capable of sequentially delivering multiple substances, according to one aspect of the present disclosure;

FIG. 13 is a cross-sectional schematic perspective view of the infusion assembly of FIG. 12;

FIG. 14 is an exploded, sectional schematic perspective view of the infusion assembly of FIG. 12;

FIG. 15 is a schematic side view of an infusion assembly, according to one aspect of the present disclosure;

FIG. 16 a cross-sectional schematic view of the infusion assembly taken along the line 16-16 of FIG. 15, illustrating a stopper piston arrangement;

FIG. 17 is a cross-sectional schematic view of the infusion assembly taken along the line 16-16 of FIG. 15, illustrating an alternative stopper piston arrangement;

FIG. 18 is a series of sectional schematic perspective views of the infusion assembly of FIG. 12, illustrating the combination of components and operation thereof;

FIG. 19 is a series of cross-sectional schematic views illustrating a dispense of multiple substances using a sequential delivery infusion assembly, according to one aspect of the present disclosure;

FIG. 20 is a cross-sectional perspective section view of a stopper piston arrangement having a penetrable portion, according to one aspect of the present disclosure;

FIG. 21 is a cross-sectional perspective section view of a stopper piston arrangement having a cavity extending entirely therethrough, according to one aspect of the present disclosure;

FIG. 22 is a cross-sectional perspective section view of a stopper piston arrangement having a seal member, according to one aspect of the present disclosure;

FIG. 23 is a schematic perspective view of plunger having a compressible stopper for use in an infusion assembly, according to one aspect of the present disclosure;

FIG. 24 is an exploded schematic perspective view of the plunger of FIG. 23;

FIG. 25 is a schematic side view of the compressible stopper of FIG. 23;

FIG. 26 is a cross-sectional schematic view of the compressible stopper of FIG. 25 taken along lines 26-26;

FIG. 27 is a cross-sectional perspective view of an infusion assembly having a nozzle received within a stopper piston in a first seating position, according to one aspect of the present disclosure;

FIG. 28 is a cross-sectional perspective view of an infusion assembly having a nozzle received within a stopper piston in a second seating position, according to one aspect of the present disclosure;

FIG. 29 is a cross-sectional section view of an infusion assembly having a nozzle received within a stopper piston in a first seating position, according to one aspect of the present disclosure;

FIG. 30 is a cross-sectional section view of an infusion assembly having a nozzle received within a stopper piston in a second seating position, according to one aspect of the present disclosure;

FIG. 31 is a magnified sectional view of the infusion assembly shown in FIG. 29; and FIG. 32 is a magnified sectional view of the infusion assembly shown in FIG. 30.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

FIGS. 1 and 2 illustrate first and second infusion devices 10, 20 used to individually infuse, deliver or otherwise administer substances to a target site. For example, first and second infusion devices 10, 20 may be used to separately infuse discrete substances into the teat of a cow during an intramammary infusion process for treatment and prevention of bovine mastitis. First infusion device 10 may be used to infuse an antibacterial substance, such as, for example, an antimicrobial product sold under the trademark SPECTRAMAST®, while second infusion device 20 may be used to infuse a physical barrier substance, such as, for example, a teat sealant product sold under the trademark ORBESEAL®. Such an infusion process is typically completed in successive steps where the first and second infusion devices 10, 20 are separately and consecutively inserted into the teat to infuse the respective product. As previously described above, however, inserting multiple infusion devices into the teat canal may increase the likelihood of a bacterial infection.

Accordingly, aspects of the present disclosure are provided to facilitate co-administration of substances in a sequential manner such that only one insertion event is needed to infuse multiple substances into a target site. Such aspects may be particularly advantageous in biological applications (both human and animal) where limiting insertion events at a target site is desirable. Furthermore, aspects of the present disclosure provide additional benefits in that the substances may also be individually administered such that the previously known process of separately infusing the substances may be practiced, if desired.

As shown in FIGS. 3-5 and 9-11, according to one aspect of the present disclosure, the first infusion device 10 may be used to form an infusion assembly 100. The infusion assembly 100 may generally include a first infusion body 110, a first nozzle 120, and a first plunger 130. The first infusion body 110 may be configured as a hollow tube or barrel for containing a first substance 25. The first plunger 130 may translate longitudinally within the first infusion body 110 so as to interact with and dispense the first substance 25 out of the first infusion body 110 through the first nozzle 120. The first nozzle 120 may be integrally formed with the first infusion body 110 so as to form a unitary structure.

According to some aspects of the present disclosure, the first plunger 130 may include a stopper piston 200 and a translating member 150. The stopper piston 200 may be separable from the translating member 150 such that the two components may be easily separated. In this regard, the stopper piston 200 may be coupled with or otherwise engaged with the translating member 150 through a snap fit. In some instances, as shown in FIGS. 4, 5, 10 and 11, the translating member may include a shaft having proximal and distal ends 135, 140. The distal end 140 may have a guide flange member 145 used to facilitate advancement of the first plunger 130. In some instances, during delivery of the first substance, the guide flange member 145 may contact and abut a first flange 170 of the first infusion body 110, thereby preventing further advancement of the plunger 130 within the first infusion body 110. The proximal end 135 may have or otherwise include a tip portion 160, which in some instances is configured similar to the first nozzle 120.

As shown in FIGS. 5 and 8, the stopper piston 200 may define a cavity 210 configured to receive the tip portion 160 of the translating member 150. In some instances, the cavity 210 may be defined so as to substantially conform to the tip portion 160 such that the stopper piston 200 can be securely connected to the translating member 150. Furthermore, the stopper piston 200 may be sized to extend outwardly within and interact with the interior walls of the first infusion body 110 such that the first substance 25 is directed toward and out of the first nozzle 120 when the first plunger 130 is advanced. The stopper piston 200 may be formed of an elastomeric material to increase performance of this function. In some instances, the stopper piston 200 may extend outwardly to substantially conform with the first infusion body 110 such that the first substance 25 cannot leak into a first chamber 165 defined by the first infusion body 110 and is instead forced out of the first nozzle 120 during advancement of the first plunger 130. In this manner, the first infusion device 10 may be used individually to infuse a single substance to a target site. Similarly, the second infusion device 20 may be used individually to infuse a single substance to a target site.

FIGS. 12-19 illustrate the infusion assembly 100 incorporating the first and second infusion devices 10, 20 so as to be capable of sequentially delivering the first substance 25 and a second substance 50 using only one insertion event into a target site (e.g., a teat canal). According to some aspects, the translating member 150 may be removed or separated from the stopper piston 200 such that a nozzle 320 of the second infusion device 20 may engage the stopper piston 200. In this manner, the second infusion device 20 may now act as the delivery means or mechanism for expelling the first substance 25 from the first infusion body 110. In this regard, the infusion assembly 100 includes a second infusion body 310, the second nozzle 320, a second plunger 330, and a second flange 370. The second infusion body 310 may define a second chamber 365 for holding the second substance 50. The second nozzle 320 may be shaped and sized to substantially correspond to the cavity 210 of the stopper piston 200. In some aspects, the second nozzle 320 may be secured to the stopper piston 200 using a snap fit configuration, or any other securement mechanism such that the stopper piston 200 is securely fixed to the second nozzle 320 and/or the second infusion body 310. The second nozzle 320 may be integrally formed with the second infusion body 310 so as to form a unitary structure.

The second plunger 330 may include a second guide flange member 345 capable of contacting and abutting the second flange 370 to limit advancement of the second plunger 330 within the second infusion body 310. Similarly, in some instances, the second guide flange member 345 may be configured to contact and abut the first guide flange member 145 to limit advancement of the second infusion body 310 and the stopper piston 200 within the first infusion body 110. The second plunger 330 may include a plunger head 380 having a second tip portion 360 configured to be received within the second nozzle 320 for maximizing dispense of the second substance 50 from the second infusion body 310. The plunger head 380 may be sized to tightly fit within the second infusion body 310 for forcing the second substance 50 out of the second infusion body 310 through the second nozzle 320.

Accordingly, the components of the first and second infusion devices 10, 20 may cooperate to form the infusion assembly 100 as a single device capable of sequential delivery, with the advantage of being separately usable for administering the first and second substances 25, 50 individually, if desired. By providing components that may be used separately or in combination, sterilization of the first and second substances 25, 50 can be achieved independently, without special procedures or extensive steps for sterilizing two separate substances stored in a single device. For example, the application of the infusion assembly 100 for treating bovine mastitis requires sterilization of the antibacterial substance and the teat sealant substance. The sterilization of these two substances requires disparate gamma radiation parameters, as previously described. As such, the individual and combinable aspects of the present disclosure allow for the storage, sterilization, and distribution of the two substances separately, but with the advantage of combining the components into a single device.

In use, as shown in FIG. 19, the infusion assembly 100 may be configured such that the translating member 150 is removed from the first infusion device 10 so that the translating member 150 is separated from the first infusion body 110. Once the translating member 150 is removed, the stopper piston 200 may remain within the first infusion body 110 such that the translating member 150 is the only part of the first plunger 130 removed from the first infusion device 10. That is, the translating member 150 may be separated from the first infusion device 10, while leaving the stopper piston 200 within the first infusion body 110. Then, the second nozzle 320 may be engaged with the stopper piston 200 within the first infusion body 110.

Alternatively, in some instances, the infusion assembly 100 may be configured such that the first plunger 130 (comprised of both the translating member 150 and the stopper piston 200) is removed from the first infusion device 10 so that the first plunger 130 is separated from the first infusion body 110. Once the first plunger 130 is removed, the stopper piston 200 may then be separated from the translating member 150. Then, the stopper piston 200 may be positioned on the second nozzle 320 of the second infusion device 20.

In any instance, the second nozzle 320 may be received within the cavity 210 of the stopper piston 200. The stopper piston 200 may be positioned against the first substance 25 contained within the first infusion body 110. The second infusion body 310 may be positioned within the first infusion body 110. In this regard, in the case of being tubular shaped, the diameter of the second infusion body 310 is less than the diameter of the first infusion body 110 such that the second infusion body 310 may be received therewithin. In this manner, a single assembly device may be formed for sequentially delivering the first and second substances 25, 50 to a target site using only a single insertion event.

With the first infusion device 10 and second infusion device 20 combined to form the infusion assembly 100, the second plunger 330 may be plunged or otherwise advanced to expel the first substance 25 from the first infusion body 110 through the first nozzle 120. In this regard, the stopper piston 200 may be forced toward the first nozzle 120 during plunging of the second plunger 330 to interact with the first substance 25, thereby forcing the first substance 25 out of the first infusion body 110. Alternatively, the second flange 370 may be advanced rather than the second plunger 330 for dispensing the first substance 25 from the first infusion body 110, as such movement will also advance the second plunger 330 toward the first nozzle 120.

After dispensing the first substance 25, the second plunger 330 may be plunged or otherwise advanced to expel the second substance 50 from the second infusion body 310 through the second nozzle 320, and then through the first nozzle 120 into the target site. The second nozzle 320 may be configured to mate within the first nozzle 120 when the second plunger 330 is in a fully plunged or fully advanced position in which the second plunger 330 cannot be advanced any further. In some instances, the second nozzle 320 may be configured to fully extend through and out of the stopper piston 200. Once the second plunger 330 is in the fully advanced position, the first and second substances 25, 50 have been sequentially delivered to the target site using only a single insertion event.

In some instances, the viscosity of the first and second substances 25, 50 may affect the operation of the device. For example, in the case of treating bovine mastitis, the teat sealant product (paste-like) may have a substantially higher viscosity than the antimicrobial product (water-like). In such instances, initially advancing the second plunger 330 forces the first substance 25 (e.g., the antimicrobial substance) out of the first nozzle 120 rather than forcing the second substance 50 (e.g., the teat sealant substance) out of the second nozzle 320 to undesirably mix with the first substance 25. Of course, in some instances, this may be avoided by sealing the end of the stopper piston 200, as discussed further below.

According to some aspects of the present disclosure, the stopper piston 200 may be sealed, non-sealed, or semi-sealed, as used to describe the requirement of the second nozzle 320 to deliver the second substance 50 to the first nozzle 120 for evacuation thereof from the infusion assembly 100. In some instances, as shown in FIG. 20, the stopper piston 200 may be sealed such that the second substance 50 cannot be delivered out of the second nozzle 320. In this regard, the stopper piston 200 may include a penetrable portion 220 capable of being pierced by the second nozzle 320 such that the second substance 50 can be delivered out of the second nozzle 320. In such instances, the stopper piston 200 may reach a point at which it cannot advance any further within the first infusion body 110, and the second plunger 330 advances the second nozzle 320 sufficiently to pierce the penetrable portion 220. The elastomeric material make-up of the stopper piston 200 may provide the flexibility to allow the second nozzle 320 to advance far enough to pierce the penetrable portion 220. As shown in FIG. 22, the stopper piston 200 may include a seal cover member 320 that may be separately attached. In such instances, the seal cover member 320 may provide the penetrable portion 220. According to some aspects, the seal cover member 320 may be wrapped about a portion or all of the stopper piston 200. In some instances, the second nozzle 320 may be configured as substantially blunt since the infusion assembly 100 may be used in an infusion procedure in contrast with procedure requiring a sharp needle to pierce an injection site.

In other instances, as shown in FIG. 21, the stopper piston 200 may be non-sealed or open such that the cavity 210 extends entirely therethrough such that the second nozzle 320 does not need to pierce any portion of the stopper piston 200 in order to facilitate delivery of the second substance 50 through the second nozzle 320. In such instances, the cavity 210 may be defined in any manner and may be defined to particularly correspond with the configuration of the second nozzle 320.

According to other aspects, as shown in FIG. 6, the stopper piston 200 may be semi-sealed in that a slit 250 may be provided, to allow the second nozzle 320 to extend through the stopper piston 200 without the need to pierce any portion thereof. That is, the stopper piston 200 may appear closed until the second nozzle 320 is advanced far enough therethrough to wedge open the slit 250. In some instances, the second nozzle 320 may not extend through the slit 250 until the stopper piston 200 is advanced to its furthest position.

In accordance with some aspects of the present disclosure, as shown in FIGS. 23-26, the stopper piston 200 may be compressible or otherwise collapsible such that a length thereof, as defined along a central axis of the cavity 210 of the stopper piston 200, may be capable of being shortened. In this manner, the second nozzle 320 may be safely disposed within the stopper piston 200 without exposure to the first substance 25 during the initial plunging action of the. In such instances, the compressible stopper piston 200 may be sealed so as to include the penetrable portion 220. Upon a stopper head 280 of the compressible stopper piston 200 reaching its most advanced position toward the first nozzle 120, the stopper head 280 interacts with the first infusion body 110. The second plunger 330 may interact with and continue to advance a stopper base 270 of the compressible stopper piston 200 such that the stopper piston 200 wherein the distance between the stopper head 280 and the stopper base 270 decreases. As such, the second nozzle 320 may extend through the stopper piston 200, and, in some instances, pierce the penetrable portion 220, such that the second substance 50 may be dispensed through the first nozzle 120.

In some instances, the compressible stopper piston 200 may include one or more structural ribs 260, each extending between the stopper base 270 and the stopper head 280 in a non-perpendicular manner. That is, the structural ribs 260 may be configured to extend angularly or in a serpentine manner between the stopper base 270 and the stopper head 280. The compressible stopper piston 200 may include cut-away portions that allow for collapsing thereof. The compressible stopper piston 200 may be made of an appropriate pliant material that permits compressing thereof. In some instances, the stopper head 280 may be dome-shaped or substantially frustoconical. The stopper head 280 may extend radially outward to circumferentially encase the first chamber 165.

According to other aspects of the present disclosure, the stopper piston 200 may be substantially non-compressible in that the stopper piston 200 is not compressed when pierced by the second nozzle 320; however, the stopper piston 200 in such instances may be resiliently-formed. In such aspects, the infusion assembly 100 may function to sequentially deliver multiple substances based on a two-stage or two-phase seating configuration or arrangement of the second nozzle 320 with respect to the stopper piston 200, as shown in FIGS. 27-32. The cavity 210 of the stopper piston 200 may define various resistance points to allow for the various seating positions or configurations of the second nozzle 320, where FIGS. 27, 29 and 31 illustrate the second nozzle 320 in a first seating position and FIGS. 28, 30 and 32 illustrate the second nozzle 320 in a second seating position.

In the first seating position, as shown in FIGS. 27, 29 and 31, the second nozzle 320 may not yet have ruptured or penetrated the penetrable portion 220 or may not have otherwise extended through the slit 250, whichever may be the case. As such, advancement of the stopper piston 200 may force the first substance 25, which in some instances may be a watery-like substance in terms of viscosity, out of the first nozzle 120. In some instances, due to the viscosity of the first substance 25, there may not be sufficient resistance by the first substance 25 to allow the second nozzle 320 to penetrate the penetrable portion 220 or slit 250 during advancement of the stopper piston 200. That is, the resistance or pressure of dispensing the first substance 25 may not be sufficient to allow the second nozzle 320 to move into the second seating position, thereby preventing the penetrable portion 220 or slit 250 from being pierced. While there may also be resistance points about the exterior of the stopper piston 200 caused by interaction of the external surfaces of the stopper piston 200 with the internal walls of the first infusion body 110, such resistance points may be configured so as to not cause the second nozzle 320 to move into the second seating position.

When the stopper piston 200 advances completely within the first infusion body 110 (i.e., the stopper head 280 meets and contacts an end wall 115 of the first infusion body 110), further advancement of the second plunger 330 may cause the second infusion body 310 to advance such that the second nozzle 320 moves into the second seating position, as shown in FIGS. 28, 30 and 32. Movement of the second nozzle 320 from the first seating position to the second seating position may cause the second nozzle 320 to penetrate the penetrable portion 220 or slit 250 and nest within the first nozzle 120 such that the second substance 50 may be expelled or dispensed from the infusion assembly 100.

The stopper piston 200 may define the cavity 210 so as to appropriately create the first and second seating positions for the second nozzle 320. According to one aspect, as shown in FIG. 31, the second nozzle 320 may include a flange 322 capable of being seated or otherwise received within a first recess 212 correspondingly configured to the flange 322. The flange 322 may abut a first abutment section 245 of the stopper piston 200 so as to provide a resistance point that allows the second nozzle 320 to advance the stopper piston 200, without piercing the penetrable portion 220 or slit 250.

Upon moving to the second seating position within the stopper piston 200, the second nozzle 320 advances within the cavity 210 so as to pierce or penetrate the penetrable portion 220 or slit 250. The second nozzle 320 may advance so as to become nested within the first nozzle 120. In the second seating position, the flange 322 and/or other components of the second nozzle 320 or second infusion body 310 may be seated or otherwise received within a second recess 214 defined by the stopper piston 200, wherein the flange 322 may abut a second abutment section 255. According to some aspects, the second recess 214 may be correspondingly defined to receive a portion of the second nozzle 320. For example, the stopper piston 200 may define an annular recess 216 for receiving the flange 322 when the second nozzle 320 is positioned in the second seating position. Additionally, the stopper piston may define a tapered recess section for receiving a correspondingly tapered section 318 of the second nozzle 320.

In some instances, a collar 312 or shoulder 314 of the second infusion body 310 may interact with internal sections of the stopper piston 200 or a back end 240 of the stopper piston 200 to form a stop such that the second nozzle 320 cannot advance any further. The back end 240 may be appropriately configured or shaped to provide sufficient clearance between the back end 240 and the collar 312 or shoulder 314 to allow enough movement by the second nozzle 320 to pierce the penetrable portion 220 or slit 250.

The stopper piston 200 may further include or otherwise define a resistance member 225, such as, for example, an integrally-formed O-ring, which resistively interacts and contacts the second nozzle 320 such that the second nozzle 320 and the second infusion body 310 remain securely engaged or intact with the stopper piston 200 once coupled. The resistance member 225 may act as an additional resistance point that allows the second nozzle 320 to advance the stopper piston 200.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An infusion assembly, comprising:
   a first infusion body having an end wall;
   a first nozzle operably engaged with the first infusion body proximate to the end wall;
   a first plunger configured to translate longitudinally within the first infusion body for dispensing a first substance out of the first infusion body through the first nozzle, the first plunger comprising a translating member and a stopper piston separable and removable from the translating member, the stopper piston defining a cavity and being configured to facilitate a two-stage seating arrangement;
a second infusion body configured to be received within the first infusion body;
a second nozzle operably engaged with the second infusion body;
a second plunger configured to translate longitudinally within the second infusion body for dispensing a second substance out of the second infusion body through the second nozzle; and
wherein the stopper piston, once separated from the translating member, is configured to receive the second nozzle in a first seating position within the cavity such that the second plunger is capable of advancing the stopper piston to dispense the first substance from the first infusion body, and the second plunger is capable of being further advanced to cause the stopper piston to abut the end wall and to move the second nozzle into a second seating position within the cavity so as to extend the second nozzle through the stopper piston such that the second substance contained in the second infusion body is capable of being dispensed through the second nozzle and the first nozzle.

2. An infusion assembly according to claim 1, wherein the stopper piston has a penetrable portion capable of being pierced so as to allow the second nozzle to extend through the penetrable portion when advanced to the second seating position.

3. An infusion assembly according to claim 2, wherein the penetrable portion comprises a slit.

4. An infusion assembly according to claim 1, wherein the translating member comprises a shaft having first and second ends, the first end having a guide surface configured to facilitate advancement of the first plunger, and the second end having a tip portion configured to conform to the cavity so as to be received therein.

5. A method of sequentially delivering a first and second substance to a target site, the method comprising:
providing a first infusion device having a first infusion body containing a first substance;
providing a second infusion device having a second infusion body containing a second substance;
positioning at least a portion of the second infusion device within the first infusion body;
engaging a second nozzle of the second infusion device with a stopper piston in a first seating position such that the second nozzle extends at least partially therethrough;
advancing a plunger associated with the second infusion device such that the stopper piston interacts with the first substance so as to expel the first substance from the first infusion body through a first nozzle of the first infusion device; and
advancing the plunger to move the second nozzle into a second seating position with respect to the stopper piston so as to pierce a penetrable portion of the stopper piston with the second nozzle such that the second nozzle extends therethrough and to expel the second substance from the second infusion body through the second nozzle and then through the first nozzle to a target site.

6. A method according to claim 5, wherein positioning at least a portion of the second infusion device within the first infusion body comprises removing an additional plunger associated with the first infusion device therefrom such that the second infusion body is capable of being received within the first infusion body.

7. A method according to claim 5, wherein the step of piercing a penetrable portion of the stopper piston further comprises piercing a penetrable portion comprising a slit.

8. A method according to claim 5, wherein the first substance is an antimicrobial formulation and the second substance is a sealant formulation.

9. A method according to claim 5, wherein the first substance is less viscous than the second substance.

10. A kit, comprising:
a first infusion device having a first substance and a first plunger, the first infusion device being configured to independently deliver the first substance to a target site via actuation of the first plunger;
a second infusion device having a second substance, a second plunger, and a nozzle, the second infusion device being configured to independently deliver the second substance to the target site via actuation of the second plunger; and
a stopper piston configured to be securely seated on the nozzle such that the second infusion device is capable of acting as a plunger for the first infusion device when the first plunger is removed, so as to expel the first substance from the first infusion device, the stopper piston having a penetrable portion, and the stopper piston defining a cavity that provides a two-stage seating arrangement to facilitate movement of the nozzle from a first seating position to a second seating position within the cavity for piercing the penetrable portion.

11. A kit according to claim 10, wherein the penetrable portion comprises a slit.

12. An infusion assembly, comprising:
a first infusion device having a first nozzle disposed proximate to an end wall, the first infusion device having a stopper piston defining a cavity and being configured to facilitate a two-stage seating arrangement;
a second infusion device configured to be received within the first infusion device, the second infusion device having a second nozzle and a plunger configured to translate longitudinally for dispensing a second substance out of the second nozzle; and
wherein the stopper piston is configured to receive the second nozzle in a first seating position within the cavity such that the plunger is capable of advancing the stopper piston to dispense a first substance from the first infusion device, and the plunger is capable of being further advanced to cause the stopper piston to abut the end wall and to move the second nozzle into a second seating position within the cavity so as to extend the second nozzle through the stopper piston such that the second substance contained in the second infusion device is capable of being dispensed through the second nozzle and the first nozzle.

13. An infusion assembly according to claim 12, wherein the stopper piston has a penetrable portion capable of being pierced so as to allow the second nozzle to extend through the penetrable portion when advanced to the second seating position.

14. An infusion assembly according to claim 13, wherein the penetrable portion comprises a slit.

* * * * *